US012602860B2

(12) United States Patent
Chen et al.

(10) Patent No.: US 12,602,860 B2
(45) Date of Patent: Apr. 14, 2026

(54) METHOD FOR CONSTRUCTING THREE-DIMENSIONAL MEDICAL IMAGE

(71) Applicant: China Medical University, Taichung City (TW)

(72) Inventors: Yi-Wen Chen, Taichung City (TW); Cheng-Ting Shih, Taichung City (TW); Kui-Chou Huang, Taichung City (TW); Hsin-Yuan Fang, Taichung City (TW); Kai-Cheng Hsu, Taichung City (TW)

(73) Assignee: China Medical University, Taichung City (TW)

( * ) Notice: Subject to any disclaimer, the term of this patent is extended or adjusted under 35 U.S.C. 154(b) by 320 days.

(21) Appl. No.: 18/336,181

(22) Filed: Jun. 16, 2023

(65) Prior Publication Data
US 2024/0013473 A1     Jan. 11, 2024

(30) Foreign Application Priority Data
Jul. 6, 2022     (TW) .................................. 111125437

(51) Int. Cl.
*G06T 15/08*     (2011.01)
*A61B 6/00*     (2006.01)
*G06T 7/50*     (2017.01)

(52) U.S. Cl.
CPC ............... *G06T 15/08* (2013.01); *A61B 6/52* (2013.01); *G06T 7/50* (2017.01); *G06T 2200/04* (2013.01); *G06T 2207/10081* (2013.01); *G06T 2207/10116* (2013.01); *G06T 2207/20081* (2013.01);
(Continued)

(58) Field of Classification Search
None
See application file for complete search history.

(56) References Cited

U.S. PATENT DOCUMENTS

2017/0042495 A1* 2/2017 Matsuzaki ............. A61B 5/055
2019/0216409 A1* 7/2019 Zhou ......................... G06T 7/11
(Continued)

FOREIGN PATENT DOCUMENTS

CN     110458799 A  * 11/2019  ........... G06T 7/0012
CN     111275130 A  *  6/2020  ............. G06N 3/045
CN     111292230 A  *  6/2020  ............. G06N 3/045
(Continued)

OTHER PUBLICATIONS

Almeida et al., Three-dimensional image volumes from two-dimensional digitally reconstructed radiographs: A deep learning approach in lower limb CT scans, Med Phys. May 2021, 48(5), May 2021, pp. 2448-2457, doi: 10.1002/mp. 14835, Epub Apr. 3, 2021, PMID: 33690903.*

*Primary Examiner* — Guillermo M Rivera-Martinez
(74) *Attorney, Agent, or Firm* — MUNCY, GEISSLER, OLDS & LOWE, P.C.

(57) ABSTRACT
A method for constructing three dimensional-medical image includes steps of inputting multiple two-dimensional images and a known three-dimensional image into a processing module and inputting a new two-dimensional image into the processing module to obtain a reconstructed three-dimensional image. The processing module utilizes a neural network to build a reconstructed three-dimensional image by unfolding the two-dimensional image to produce a three-dimensional reconstruction.

4 Claims, 7 Drawing Sheets

2D X-ray

3D CT Volume

(52) U.S. Cl.
CPC ............... *G06T 2207/20084* (2013.01); *G06T 2207/30004* (2013.01); *G06T 2210/41* (2013.01)

(56) References Cited

U.S. PATENT DOCUMENTS

| | | | | |
|---|---|---|---|---|
| 2020/0401854 | A1* | 12/2020 | Peng ................... | G06F 18/2148 |
| 2021/0334958 | A1 | 10/2021 | Siow et al. | |

FOREIGN PATENT DOCUMENTS

| | | |
|---|---|---|
| CN | 113506334 A | 10/2021 |
| CN | 114240824 A | 3/2022 |
| CN | 114299078 A | 4/2022 |
| CN | 114332378 A | 4/2022 |
| TW | 202141517 A | 11/2021 |

* cited by examiner

3D CT Volume

2D X-ray

Difference images

CT recon from X-ray

X-ray

Original CT

METHOD FOR CONSTRUCTING THREE-DIMENSIONAL MEDICAL IMAGE

FIELD OF INVENTION

The present invention relates generally to a method for converting two-dimensional medical images into three-dimensional medical images.

BACKGROUND OF THE INVENTION

Medical imaging technology is an essential component of modern medicine. Among them, magnetic resonance imaging (MRI) and computed tomography (CT) are the most commonly used three-dimensional medical imaging techniques.

Three-dimensional medical imaging has become an indispensable tool for physicians in understanding the intricacies of human tissue and diagnosing diseases. Furthermore, three-dimensional medical imaging capabilities are crucial in assisting doctors in identifying the location of symptoms and obtaining detailed pathological information. While common three-dimensional medical imaging techniques offer various benefits, they are somewhat inconvenient and relatively expensive compared to traditional X-ray imaging. Additionally, common three-dimensional medical imaging techniques, such as CT, expose patients to significant radiation doses, while MRI suffers from much longer imaging times. These are the primary challenges that need to be addressed and improved upon for three-dimensional imaging to reach its full potential.

SUMMARY OF THE INVENTION

To solve abovementioned problems, this present invention discloses a method for constructing three-dimensional medical image comprising steps of: inputting multiple two-dimensional images and a known three-dimensional image into a processing module, wherein: the two-dimensional images comprise multiple characteristic parameters corresponding to a specific body part and the known three-dimensional image comprises the image of the specific body part, wherein an X-ray module generates the two-dimensional images; and the processing module generates a neural network through a deep learning algorithm with reference to the known three-dimensional image and unfolding the two-dimensional images to produce a three-dimensional reconstruction; and inputting a new two-dimensional image into the processing module to obtain a reconstructed three-dimensional image, wherein the processing module utilizes the neural network to build the reconstructed three-dimensional image by unfolding the new two-dimensional image to produce a three-dimensional reconstruction.

Wherein, the X-ray module further comprises a distance calculation module measuring and calculating the characteristic parameters, wherein the characteristic parameters comprise a projection angle corresponding to the body part, a distance between a light source and the body part, a distance between the imaging device and the body part, or a front view or a back view orientation.

Wherein, the deep learning algorithm in the processing module extracts information from the two-dimensional image and reconstructs the reconstructed three-dimensional image, wherein the two-dimensional image is processes with a convolutional layer, batch normalization, and an activation layer to preliminarily extract features and filter out important features, and a residual module is used to further extract features and incorporate the important features from the previous layer of the deep neural network, and the convolutional layer is set with a stride of 2, and a scale of the important features in X and Y directions is reduced while simultaneously increasing the scale in the Z direction, and a number of kernels is increased to accommodate various types of feature extraction responses, and the process is repeated multiple times, and the important features are synthesized onto the known three-dimensional image using the residual module, and a transposed convolutional layer with a stride of 2 is used to enlarge the scale of the important features in the X and Y directions while reducing the scale in the Z direction, and the process is repeated until the size of the important features matches the volume of the three-dimensional known image.

DETAILED DESCRIPTION OF THE PREFERRED EMBODIMENTS

Figure 1:
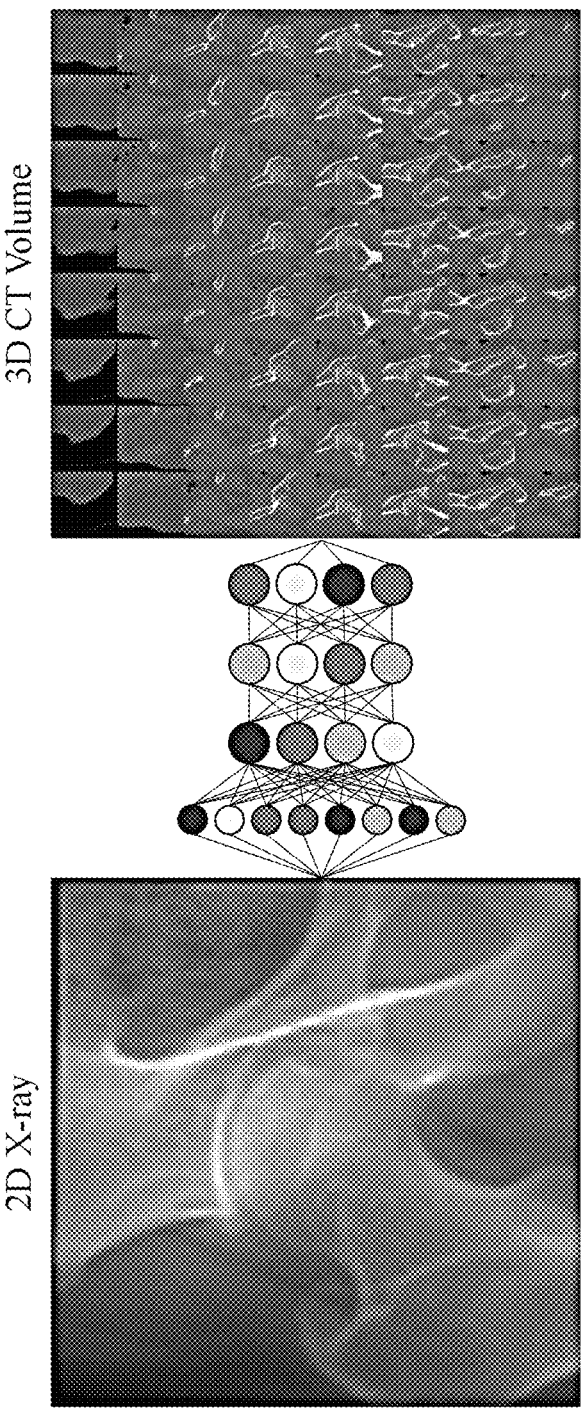
FIG. 1 is a schematic diagram of a preferred embodiment of a system in accordance with this invention.
Figure 2:
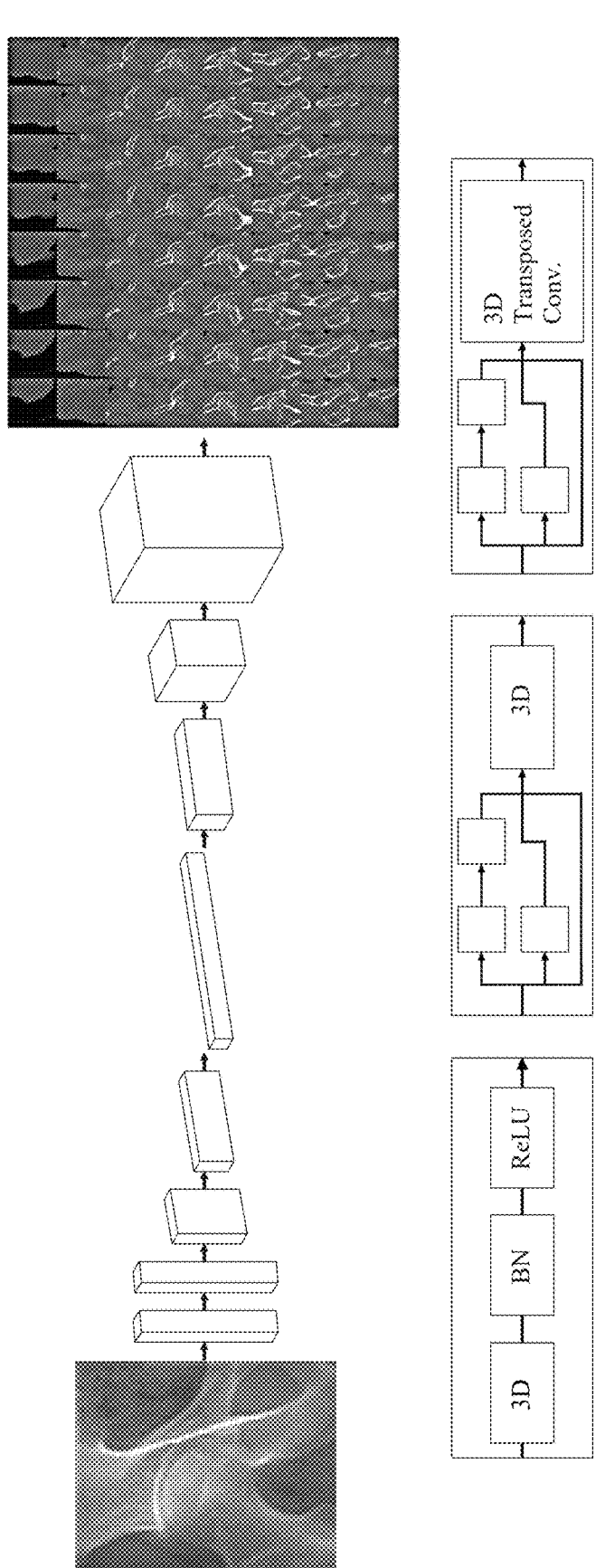
FIG. 2 is a schematic diagram of a preferred embodiment of converting a two-dimensional medical image into a three-dimensional medical image in accordance with this invention.
Figure 5:
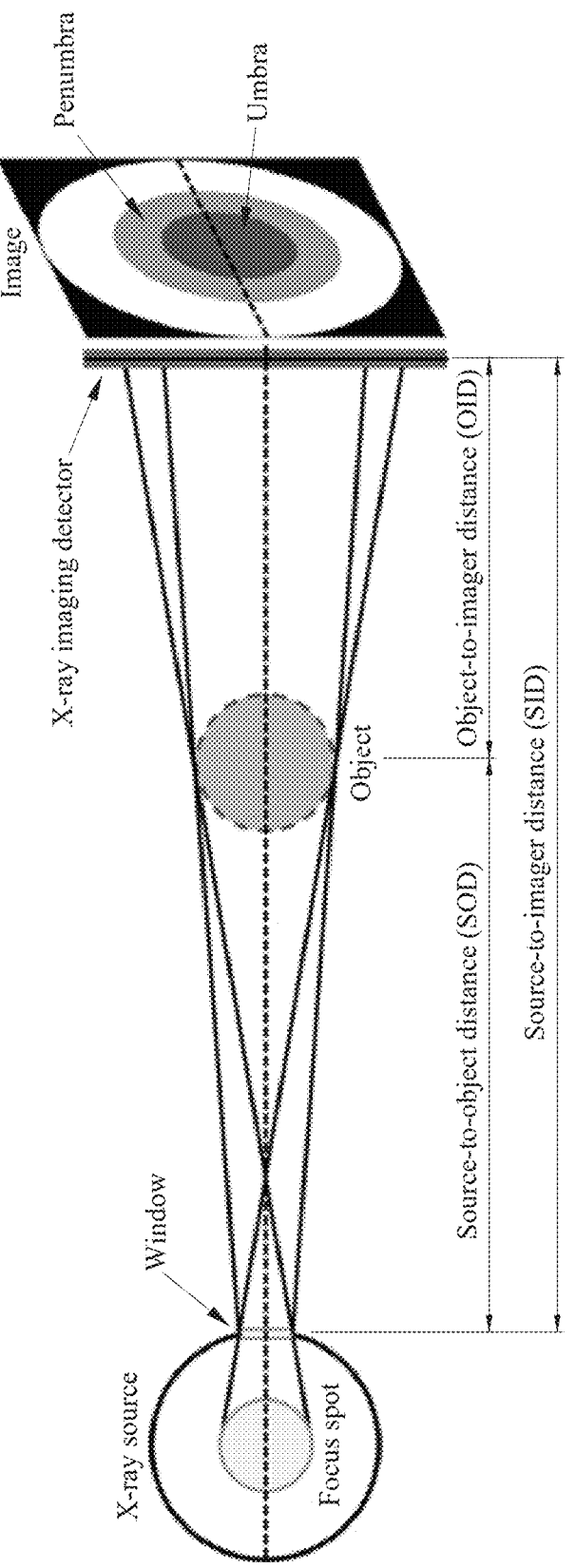
FIG. 5 is a schematic diagram of a preferred embodiment of an X-ray module in accordance with this invention.
Figure 6:
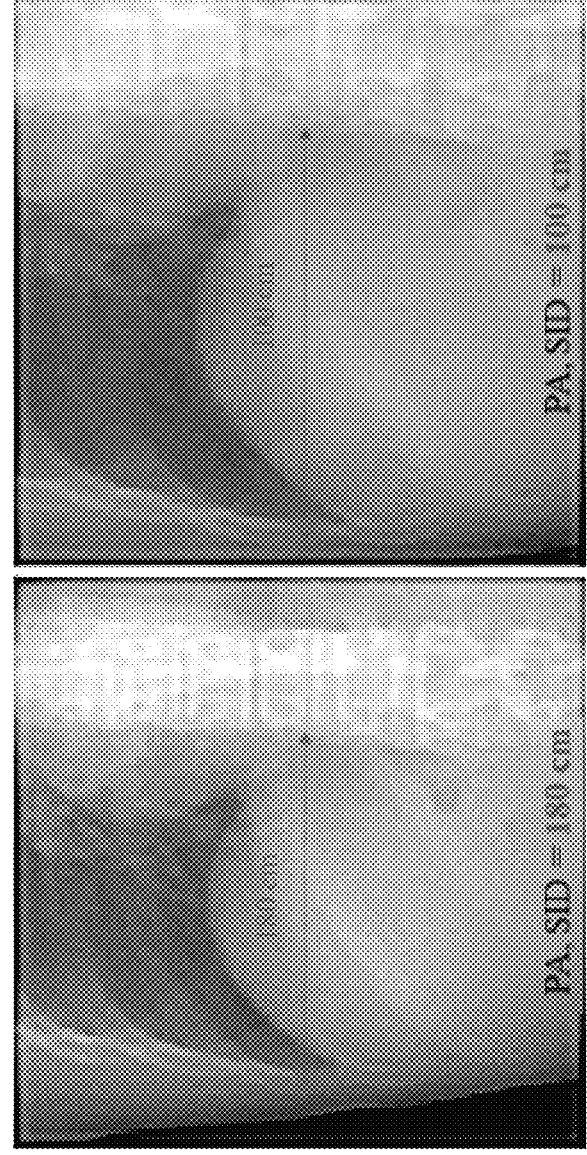
FIG. 6 shows two diagrams for a comparison of two three-dimensional medical images with different OID.

With reference to FIG. 1, FIG. 2, and FIG. 5, a preferred embodiment of a method for constructing three-dimensional medical imaging in accordance with this invention includes the following steps:

STEP 1: Generating a two-dimensional image with an X-ray module. The X-ray module includes an X-ray tube and an image receptor. The X-ray tube emits X-ray waves, while the image receptor detects the intensity of the X-ray waves. The X-ray module also incorporates a distance calculation module. The distance calculation module calculates multiple characteristic parameters of the two-dimensional image. For example, the distance calculation module calculates the source-spray distance and the spray-detector distance of the two-dimensional image. The source-spray distance refers to the distance between the X-ray source and the image receptor (source to image receptor distance, abbreviated as SID), while the spray-detector distance refers to the distance between the subject being imaged and the image receptor (object to image receptor distance, abbreviated as OID). The distance calculation module obtains magnification information through the source-spray distance. The distance calculation module comprises multiple sensors to precisely measure or calculate the characteristic parameters.

STEP 2: During the learning phase, multiple said two-dimensional images of a specific region are fed into a processing module. Multiple said two-dimensional images with similar or adjacent regions, containing various characteristic parameters, are inputted into the processing module. The processing module comprises a high-throughput and multi-threaded hardware architecture.

With reference to FIG. 5, based on principles of imaging, an ideal source of X-ray form the X-ray tube can be considered as an infinitesimally small point source. Therefore, when this X-ray penetrates through a human body, it forms an image on the image receptor. Different characteristic parameters, such as the source-spray distances and the spray-detector distances of the two-dimensional images will result in different imaging outcomes, and thus presenting varying degrees of geometric distortions and magnification ratios on the two-dimensional images. In this step, a large amount of the two-dimensional images with known characteristic parameters are fed to the processing module. Preferably, the two-dimensional images possess similar characteristic parameters (i.e., the two-dimensional images have similar projection conditions). In this step, a large quantity of the two-dimensional images with different projection angles, source-spray distances, spray-detector distances, and front, back, or lateral views are obtained and inputted to the processing module.

For example, in this step, the two-dimensional images are obtained by capturing X-ray images with the X-ray module from different patients with varying characteristic parameters. For instance, multiple patients' knee joints are captured by taking the two-dimensional images from various perspectives. This includes capturing images from the front, the back, and the lateral views, as well as with different projection angles (f 5 degrees in the forward direction and ±5 degrees in the backward direction).

The reason of inputting a great amount of the two-dimensional images with different known characteristic parameters is because the X-ray imaging process can result in varying geometric deformations of the final image (umbra, penumbra) due to the difference of the characteristic parameters of the two-dimensional images. By inputting and learning from a large quantity of the different two-dimensional images, the processing module can extract internal anatomical information with higher precision. Preferably, the characteristic parameters of each two-dimensional image are also inputted, thus a more accurate extraction of internal anatomical information of the two-dimensional images by the processing module can be achieved. Furthermore, the two-dimensional images with shorter spray-detector distances are preferred, as they tend to exhibit less geometric deformation.

Figure 7:
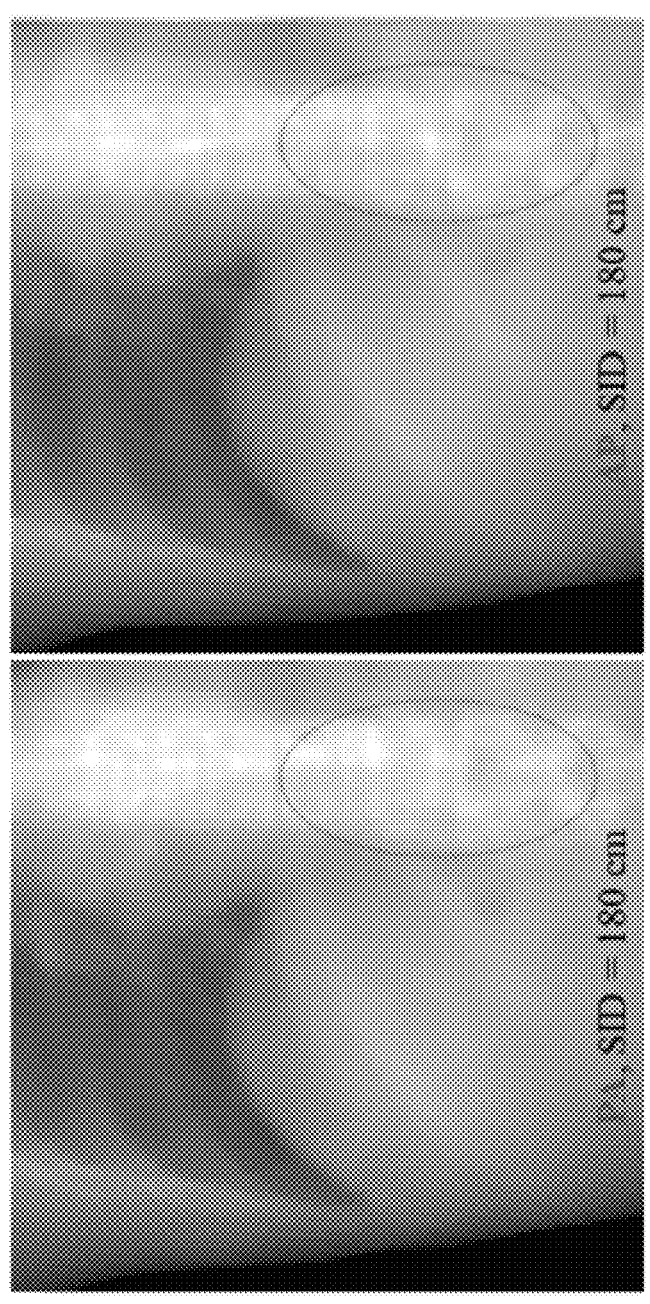
FIG. 7 shows to diagrams for a comparison of two three-dimensional medical images, one image with PA view and the other with AP view.

With reference to FIG. 7, regarding the front, back, or lateral view images, capturing both the front and back views of a specific body part provides different information within the two-dimensional images. By analyzing the imaging results, such as the varying degrees of geometric deformation, through learning, it is possible to infer and differentiate between the front and back view images based on the two-dimensional images. In the context of this invention, the terms "front view" and "back view" refer to the orientation of capturing a specific body part. For example, when capturing the two-dimensional images of a chest of a patient, the orientation of capturing the two-dimensional images can be either in a poster-anterior view (PA view) or in an anterior-poster view (AP view) as shown in FIG. 7, and the PA view is defined as the front view and the AP view is then defined as the back view.

STEP 3: The processing module determines to enter the validation phase or to enter the three-dimensional image generation mode. The processing module receives instructions from a user to select either the validation phase or the three-dimensional image generation mode. If the validation phase is chosen, the processing module proceeds with STEP 4. If the three-dimensional image generation mode is selected, the module executes STEP 5.

STEP 4: The processing module takes the specific two-dimensional images and a known three-dimensional image of the particular body part and utilizes deep machine learning techniques to extract information from the two-dimensional image to generate a three-dimensional reconstructed image. In this step, the inputted two-dimensional image enters a convolutional layer, is followed by batch normalization, and finally enters an activation layer (ReLU activation). This process aims to extract initial features from the two-dimensional image and filters out important features of the two-dimensional image. Batch normalization is applied to the three-dimensional image by rotating the three-dimensional image (e.g., a CT image) volume to align with the orientation of the two-dimensional image. From the image volume, a specific region of size, for example, 128×128×128, is extracted, and the corresponding two-dimensional image within the same irradiation range becomes a selected two-dimensional image for further processing. In this step, paired training data can be generated during the learning phase, consisting of both three-dimensional and two-dimensional images. Preferably, 80% of the two-dimensional images are used for training, while the remaining 20% of two-dimensional images are used for validating the training results. This ensures that the model is trained on a large and diverse dataset and can be effectively evaluated for its performance.

The deep machine learning process involves training a deep neural network. Once the architecture of the network is constructed, the Adaptive Moment Estimation (Adam) optimizer is used for iterative learning of the filter kernels in the network. The learning rate is set to 10-5, the number of training epochs is set to 100, and the batch size is set to 2. After extracting the important features, a residual block algorithm is applied to further extract features. The important features of previous layers are added back into the network. Then, a convolutional layer with a stride of 2 is used to reduce the scale of the important features in the X and Y directions while simultaneously enlarging the scale in the Z direction. The number of kernels is also increased to accommodate the extraction of various types of feature responses. This process is repeated multiple times until the desired scale and the number of kernels are achieved.

Then, the important features on the known three-dimensional image are synthesized by using the residual block. A transposed convolutional layer with a stride of 2 is then used to enlarge the scale of the important features in the X and Y directions while simultaneously reducing the scale in the Z direction. This step is repeated until the size of the important features matches the volume size of the known three-dimensional image. Preferably, the known three-dimensional image can be a computed tomography (CT) scan image.

Based on the previous explanation, this step of machine learning involves building a neural network that can reconstruct a three-dimensional image from a two-dimensional image in the future. The purpose is to enable subsequent input of two-dimensional images to be transformed into corresponding three-dimensional reconstructed images through the established neural network and the learned results.

As described above, the machine learning in this step involves creating a neural network capable of reconstructing three-dimensional images from the two-dimensional images. The purpose of this step is to enable the conversion of subsequent inputted two-dimensional images into their corresponding three-dimensional reconstructed images with the established neural network and the acquired learning results.

STEP 5: Inputting unknown two-dimensional images into the processing module, extracting information from the unknown two-dimensional images, and generating corresponding three-dimensional reconstructed images by the processing module. The two-dimensional image inputted into the processing module first passes through a convolutional layer and then is subjected to batch normalization. Finally, the two-dimensional images are fed into an activation layer to extract initial features and filter out important features. Once these important features are extracted, a residual block is utilized to further extract features. Important features of the previous layers are added back to the network, and a convolutional layer with a stride of 2 is employed to reduce the scale of the important features in the X and Y directions while simultaneously magnifying them in the Z direction. The number of kernels is also increased to accommodate various types of feature extraction responses. This process is repeated multiple times until the appropriate scale and the number of kernels are achieved. Finally, the important features are synthesized using the residual block to reconstruct the three-dimensional image.

Figure 3:
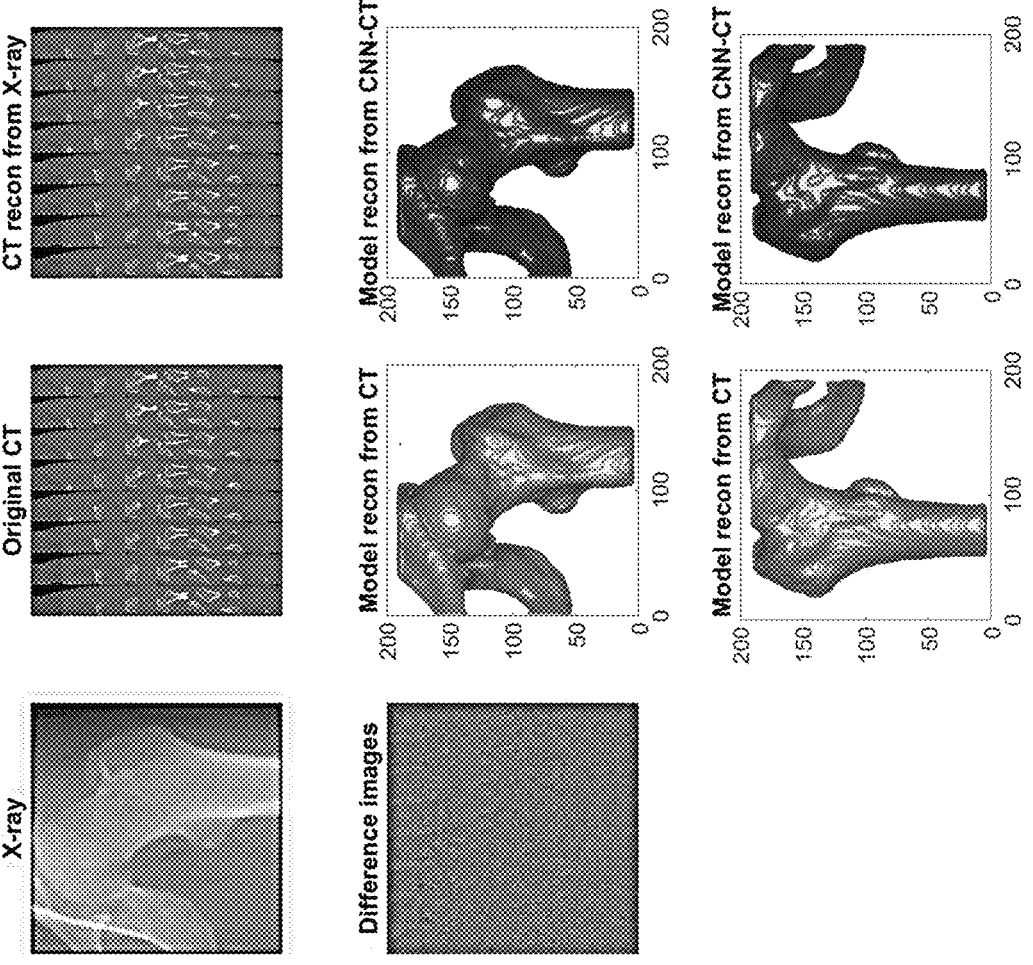
FIG. 3 shows multiple diagrams for comparisons of multiple three-dimensional medical images in accordance with this invention with a three-dimensional medical image generated from CT.
Figure 4:
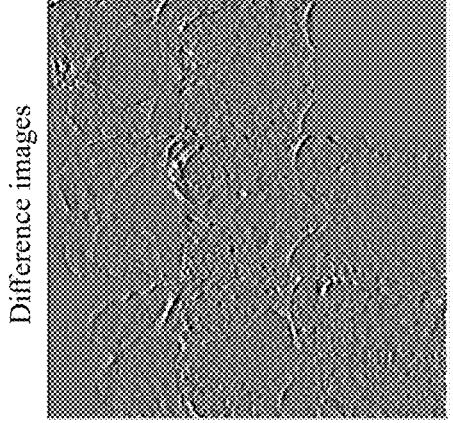
FIG. 4 shows multiple diagrams for comparisons of a three-dimensional medical image in accordance with this invention with a three-dimensional medical image generated from CT.
Figure 4:
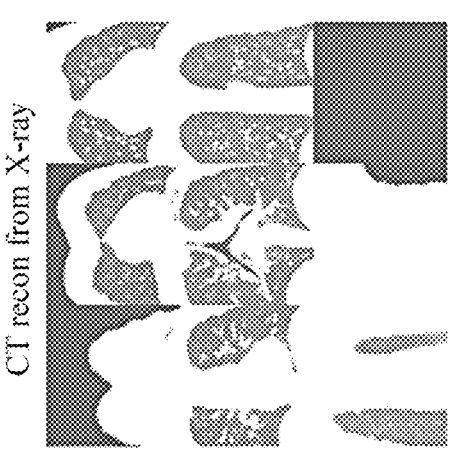
Figure 4:
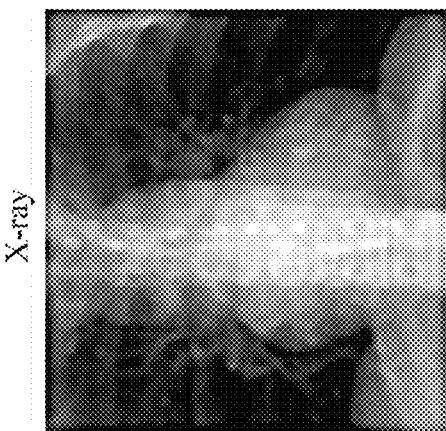
Figure 4:
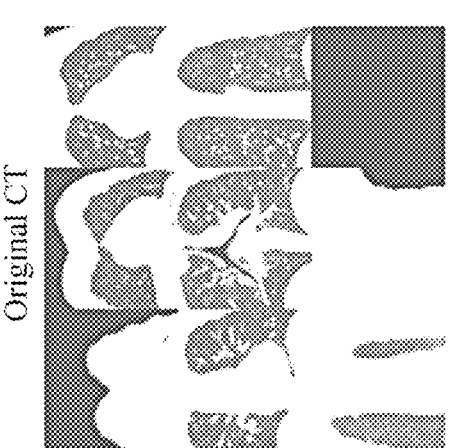

With reference to FIG. 3 and FIG. 4, the two-dimensional image (X-ray image), the original known three-dimensional image (Original CT image), the reconstructed three-dimensional image (CT recon from X-ray), and the difference images between the three-dimensional known image and the three-dimensional reconstructed image are illustrated. The difference images have low contour visibility, due to the lack of significant difference between the three-dimensional known image and the three-dimensional reconstructed image, which means the reconstructed three-dimensional image (CT recon from X-ray) has high similarity with three-dimensional image (Original CT image). The analysis results as above can be clear obtained in FIG. 4A, since the number of image requirements is relatively fewer, the difference images in FIG. 4 present higher contour visibility compared to the difference images in FIG. 3, indicating a light difference between the three-dimensional known image and the three-dimensional reconstructed image in FIG. 4.

In this embodiment, the steps of the aforementioned machine learning enable the automated reconstruction of the two-dimensional images containing depth information into three-dimensional reconstructed images. During the training process, special consideration was given to inputting two-dimensional images captured under different imaging conditions to significantly improve the accuracy of the reconstruction.

In practical applications, during the training phase, a large number of the two-dimensional images and corresponding known three-dimensional images from various body parts (such as a chest, a pelvis, etc.) captured at different angles are analyzed separately. The characteristic parameters obtained during the two-dimensional image capturing process are used as the basis for the processing module to learn to reconstruct a three-dimensional image. In the deep learning process, each layer of the network can expand the dimensions gradually from one layer to the next, for example, $2 \rightarrow 4 \rightarrow 8 \rightarrow 16$, to achieve the construction of the three-dimensional reconstructed image.

Due to X-ray geometric distortion, different geometric deformations can occur depending on the variation of the characteristic parameters used during image capture. For example, different angles and orientations can result in distance difference of the human tissue to the X-ray source in the two-dimensional image. In the training phase, a significant number of the three-dimensional image references are provided to compare and assess the reconstruction of the constructed three-dimensional image with the actual three-dimensional image, confirming the learning results and accuracy.

Based on the aforementioned description, the present invention has the following advantages:

1. A method for converting two-dimensional X-ray images into a three-dimensional image, which incorporates considerations of geometric deformations in the two-dimensional images during the deep learning process. For example, information is extracted with the use of convolutional layers, and the thickness of the two-dimensional images is gradually increased to generate the final three-dimensional reconstructed image.

2. The present invention utilizes a deep learning neural network proposed herein to effectively reconstruct human tissue information from a single X-ray image. The average absolute percentage error for the reconstructed images is 3.71%, and the average absolute percentage error for all validation cases is 4.16%. These results demonstrate that the deep neural network trained using this method can accurately reconstruct three-dimensional human body tissue images corresponding to the X-ray imaging range.

3. The present invention addresses the technical issues in prior art where the reconstruction of a two-dimensional image requires the use of external positioning information (such as reference coordinates) or the input of two-dimensional images taken from different angles in order to create a reconstructed three-dimensional image. The present invention achieves the unexpected result of reconstructing a three-dimensional image solely from a single two-dimensional image, without the need for additional positioning information or multiple angle images.

What is claimed is:

1. A method for constructing three-dimensional medical image comprising steps of:

inputting multiple two-dimensional images and a known three-dimensional image into a processing module, wherein:

the two-dimensional images comprise multiple characteristic parameters corresponding to a specific body part and the known three-dimensional image comprises an image of the specific body part, wherein an X-ray module generates the two-dimensional images; and the processing module generates a neural network through a deep learning algorithm with reference to the known three-dimensional image and unfolding the two-dimensional images to produce a three-dimensional reconstruction; and inputting a new two-dimensional image into the processing module to obtain a reconstructed three-dimensional image, wherein the processing module utilizes the neural network to build the reconstructed three-dimensional image by unfolding the new two-dimensional image to produce the three-dimensional reconstruction.

2. The method for constructing three-dimensional medical image according to claim 1, wherein the X-ray module further comprises a distance calculation module measuring and calculating the characteristic parameters, wherein the characteristic parameters comprise a projection angle corresponding to the specific body part, a distance between a light source and the specific body part, a distance between the imaging device and the body part, or a front view or a back view orientation.

3. The method for constructing three-dimensional medical image according to claim 1, wherein the deep learning algorithm in the processing module comprising a first process and a second process, wherein:

the first process comprises steps of extracting information from the two-dimensional images and reconstructing the reconstructed three-dimensional image, wherein the two-dimensional image or the new two-dimensional image is processes with a convolutional layer, batch normalization, and an activation layer to preliminarily extract features and filter out important features, and a residual module is used to further extract features and incorporate the important features from the previous layer of the deep neural network, and the convolutional layer is set with a stride of 2, and a scale of the important features in X and Y directions is reduced while simultaneously increasing the scale in the Z direction, and a number of kernels is increased to accommodate various types of feature extraction responses;

the second process comprises steps of synthesizing the important features onto the known three-dimensional image using the residual module, and using a transposed convolutional layer with a stride of 2 to enlarge the scale of the important features in the X and Y directions while reducing the scale in the Z direction; and the processing module repeats the first process and the second process until the size of the important features matches the volume of the three-dimensional known image.

4. The method for constructing three-dimensional medical image according to claim 2, wherein the deep learning algorithm in the processing module comprising a first process and a second process, wherein:

the first process comprises steps of extracting information from the two-dimensional images and reconstructing the reconstructed three-dimensional image, wherein the two-dimensional image or the new two-dimensional image is processes with a convolutional layer, batch normalization, and an activation layer to preliminarily extract features and filter out important features, and a residual module is used to further extract features and incorporate the important features from the previous layer of the deep neural network, and the convolutional layer is set with a stride of 2, and a scale of the important features in X and Y directions is reduced while simultaneously increasing the scale in the Z direction, and a number of kernels is increased to accommodate various types of feature extraction responses;

the second process comprises steps of synthesizing the important features onto the known three-dimensional image using the residual module, and using a transposed convolutional layer with a stride of 2 to enlarge the scale of the important features in the X and Y directions while reducing the scale in the Z direction; and the processing module repeats the first process and the second process until the size of the important features matches the volume of the three-dimensional known image.

* * * * *